US006475518B1

(12) United States Patent
Baumgart et al.

(10) Patent No.: US 6,475,518 B1
(45) Date of Patent: Nov. 5, 2002

(54) METHODS AND COMPOSITIONS FOR TREATMENT OF DISORDERS ASSOCIATED WITH CHLAMYDIA AND SIMILAR BACTERIAL INFECTION

(76) Inventors: Karl William Baumgart, 66 Pacific Highway, St. Leonards, NSW 2065 (AU); Thomas Julius Borody, 144 Great North Road, Five Dock, NSW 2046 (AU)

( * ) Notice: Subject to any disclaimer, the term of this patent is extended or adjusted under 35 U.S.C. 154(b) by 0 days.

(21) Appl. No.: 09/736,029

(22) PCT Filed: Jun. 20, 1999

(86) PCT No.: PCT/AU99/00528

§ 371 (c)(1),
(2), (4) Date: Feb. 1, 2001

(87) PCT Pub. No.: WO00/01378

PCT Pub. Date: Jan. 13, 2000

(30) Foreign Application Priority Data

Jun. 30, 1998 (AU) .......................................... PP4376/98

(51) Int. Cl.⁷ ................................................. A61K 9/48
(52) U.S. Cl. ...................................................... 424/451
(58) Field of Search ........................ 514/312; 546/153, 546/154; 424/234.1, 263.1, 264.1

(56) References Cited

U.S. PATENT DOCUMENTS 6,080,757 A * 6/2000 Brown ....................... 514/312

FOREIGN PATENT DOCUMENTS

| GB | 1463550 | | 2/1977 |
| GB | 1 463 550 | * | 2/1977 |
| GB | WO 96/33670 | * | 10/1996 |
| WO | 96/33670 | | 10/1996 |

OTHER PUBLICATIONS

Bedos, J. P., et al., Presse Medicale 27(28), 1440–1441 (Sep. 26, 1998).

Pichichero, M. E., Annals of Emergency Medicine 25 (3), 390–403 (3/95).

Bowie, W. R., Infection 10, Suppl. 1, S46–52 (1982).

Bowie, W. R., et al., The Lancet 2 (7998), 1276–1278 (12/76).

Bowie, W. R., et al., Drugs 27 (5), 459–468 (1984).

Patent Abstracts of Japan C311, p. 311, JP–60120815 (A) (Jun. 28, 1985).

* cited by examiner

Primary Examiner—Michael G. Hartley
Assistant Examiner—Konata M. George

(57) ABSTRACT

At least two different antibiotics are administered to treat condition associated with infection by *Chlamydia* species, *Mycoplasma* species, *Listeria* species and *Bartonella* species, and the aetiologic agents of leptospirosis and Q fever. Compositions comprise the antibiotics.

31 Claims, No Drawings

METHODS AND COMPOSITIONS FOR TREATMENT OF DISORDERS ASSOCIATED WITH CHLAMYDIA AND SIMILAR BACTERIAL INFECTION

PRIORITY INFORMATION

This is a 371 of PCT/AU/00528, filed Jun. 30, 1999 and claims convention priority from Australian Provisional Application No. PP4376, filed Jun. 30, 1998; PCT/AU/00528 has been published under No. WO 00/01378 on Jan. 13, 2000 and the publication is in English. A Demand for Chaper II was filed in PCT/AU/00528.

TECHNICAL FIELD

The invention relates to pharmaceutical compositions and methods for the treatment of vascular disease and other diseases either resulting from, aggravated by or associated with infection by *Chlamydia pneumoniae*, other *Chlamydia* species and similar susceptible microorganisms.

BACKGROUND OF THE INVENTION

Vascular disease remains a major cause of morbidity and mortality worldwide. The development of atheromatous plaque within vessel walls followed by complications such as plaque rupture with activation of the clotting cascade and occlusion of the vessel resulting in infarction of distant tissue accounts for the majority of myocardial infarction, ischaemic stroke and other ischaemic tissue injury. Conventional therapy for vascular disease seeks to prevent or reverse clot formation or to reduce vascular disease risk factors such as dyslipidaemia or hypertension. *Chlamydia pneumoniae* is a recently described microorganism, which has been identified in atherosclerotic plaque and incriminated in vascular disease. It is an obligate intracellular pathogen that grows within macrophages and endothelial cells. Infection with *C. pneumoniae* is characterised by intracellular persistence following infection. Approximately 50% of the population are seropositive for *C. pneumoniae* in adult life and most persons acquire the infection by the respiratory route. Not all persons infected with *C. pneumoniae* develop vascular disease, however. Recovery rates of the microorganism have ranged between 20 to 60% of sites of atherosclerotic tissue and the organism has not been recovered from normal vascular tissue. Animal models have been developed in which infection with *C. pneumoniae* is followed by the development of atherosclerotic plaque. To date, however, Koch's postulates have not been fulfilled for *C. pneumoniae* in human atherosclerotic vascular disease, and this is in part a consequence of the serious nature of challenge testing as well as the fact that the organism is an obligate intracellular pathogen. Two limited therapeutic studies have been published in which there appears to be a benefit after monotherapy with a macrolide antibiotic. In one of these studies (Gupta S, et al., *Circulation* 1997, 96, 404–407) azithromycin was used, and the benefit was not sustained after initial therapy. In the other study (Gurfinkel E, et al., *Lancet* 1997, 350, 404–407) roxithromycin was used as sole therapy and in limited numbers a benefit was described, although prolonged follow-up has not yet been reported. In another study (Sinisalo J, et al., *J. Antimicrob. Chemother.* 1998, 41, 85–92) tetracycline antibiotics were used as monotherapy and no clinical benefit was discerned.

In the case of "difficult to eradicate" intracellular pathogens, widespread use of single antibiotic regimes has serious potential adverse consequences for the population at large as well as for individuals who may develop resistant infections. Important examples of these problems in other areas of clinical practice include tuberculosis, leprosy and *Helicobacter pylori* infections. A further feature of largely intracellular infections such as those in which combination regimes have come to be used relates to the concept of "suppression" versus "eradication" following treatment. Although a course of macrolides in the treatment of *C. pneumoniae* can result in seemingly measurable early improvement clinically, the patients remain at risk of developing a recrudescence of the intracellular infection which has been merely suppressed rather than eradicated. With regrowth of the bacteria, the disease returns and the likelihood of response to repeated therapy is diminished, with the spectre of antimicrobial resistance. Furthermore, widespread use of single antibiotic regimes may result in greater resistance amongst *C. pneumoniae* and other important human pathogens than those being treated. Until now it has not been realised that antibiotic monotherapy which could result in a transient improvement in clinical parameters, was actually an indication of the suppression of the bacterial growth, with probable entry of the bacteria into a more intracellular yet chronic phase of infection.

There is therefore a need for methods of treating conditions associated with infection by *C. pneumoniae* and similar susceptible microorganisms which treat the initial infection so as to prevent the chronic phase of infection with its consequences of ongoing disease and heightened bacterial resistance.

The present inventors have found that a multi-drug therapy regimen is well tolerated and has a superior clinical efficacy in resolution of infections caused by *Chlamydia* species and similar susceptible microorganisms, and particularly *C. pneumoniae*, compared to monotherapy. Indeed, the method of treatment of the present invention is more likely to cure the infection rather than simply suppress it and is more likely to prevent the development of resistant isolates.

The use of multiple antibiotics for *C. pneumoniae* infection had not been studied prior to the date of the present invention. Experts in the field who have initiated clinical trials before and after the date of the present invention have only used single agent regimes. Prior to the date of the present invention, it had not been considered necessary or desirable to use multiple antibiotic regimes for the treatment of *Chlamydia pneumoniae*, other *Chlamydia* species and similar susceptible microorganisms. Furthermore, although there have been therapies for such infections in the past which have been considered adequate in the past, the present inventors have observed that with the passage of time there has been a change of bacterial susceptibility in communities towards more "difficult-to-cure" infections requiring the invention and development of more aggressive, yet safe, therapies. It is an object of the present invention to provide one such improved therapy.

SUMMARY OF THE INVENTION

Accordingly, in a first embodiment the present invention provides a method for the treatment or prevention of a condition associated with infection by *Chlamydia* species or similar susceptible microorganisms in a patient in need of such treatment or prevention, the method comprising the administration to the patient of an effective amount of at least two different antibiotics or antimicrobial agents selected from the group consisting of tetracyclines, macrolides, quinolones, chloramphenicol, rifamycins, sulfonamides, co-trimoxazole and oxazolidinones.

Throughout the present specification, "similar susceptible microorganisms" are defined as including other difficult to culture, "atypical" agents such as *Mycoplasma* species, *Listeria* species, *Bartonella* species, and the aetiologic agents of Leptospirosis and Q fever.

The present invention also provides the use of at least two different antibiotics or antimicrobial agents selected from the group consisting of tetracyclines, macrolides, quinolones, chloramphenicol, rifamycins, sulfonamides, co-trimoxazole and oxazolidinones for the manufacture of a medicament for the treatment or prevention of a condition associated with infection by *Chlamydia* species or similar susceptible microorganisms in a patient in need of such treatment.

The present invention further provides at least two different antibiotics or antimicrobial agents selected from the group consisting of tetracyclines, macrolides, quinolones, chloramphenicol, rifamycins, sulfonamides, co-trimoxazole and oxazolidinones, when used for the treatment or prevention of a condition associated with infection by *Chlamydia* species or similar susceptible microorganisms in a patient in need of such treatment.

In a second embodiment, the invention provides a pharmaceutical composition for the treatment or prevention of a condition associated with infection by *Chlamydia* species or similar susceptible microorganisms in a patient in need of such treatment or prevention, the pharmaceutical composition comprising at least two different antibiotics or antimicrobial agents selected from the group consisting of tetracyclines, macrolides, quinolones, chloramphenicol, rifamycins, sulfonamides, co-trimoxazole and oxazolidinones.

In a third embodiment, the invention provides a pharmaceutical composition comprising a first antibiotic or antimicrobial agent and at least a second antibiotic or antimicrobial agent wherein at least one of said antibiotics or antimicrobial agents is provided with a pharmaceutically acceptable coating, said antibiotics or antimicrobial agents being selected from the group consisting of tetracyclines, microlides, quinolones, chloramphenicol, rifamycins, sulfonamides, co-trimoxazole and oxazolidinones.

In a fourth embodiment, the invention provides a process for preparing a pharmaceutical composition, the process comprising providing a first antibiotic or antimicrobial agent with a first pharmaceutically acceptable coating and providing at least a second antibiotic or antimicrobial agent, optionally with a second pharmaceutically acceptable coating, and incorporating the coated first antibiotic or antimicrobial agent and the optionally coated second antibiotic or antimicrobial agent into a single dosage form, said antibiotics or antimicrobial agents being selected from the group consisting of tetracyclines, macrolides, quinolones, chloramphenicol, rifamycins, sulfonamides, co-trimoxazole and oxazolidinones.

The invention also provides a pharmaceutical composition when prepared by the process of the fourth embodiment.

In further embodiments, the invention provides a method of the first embodiment which further includes the administration of a third, or a third and a fourth, or a third, a fourth and one or more further different antimicrobial agents or antibiotics. Similarly, the invention provides a pharmaceutical composition of the second embodiment which includes a third, or a third and a fourth, or a third, a fourth and one or more further different antimicrobial agents or antibiotics.

DETAILED DESCRIPTION OF THE INVENTION

Throughout this specification, the word "comprising" is to be understood to mean "including principally, but not necessarily solely". Variants such as "comprise" or "comprises" are to be understood to have corresponding meanings.

The present invention provides methods and pharmaceutical compositions for treating patients either with, or at risk of, vascular disease following infection with *C. pneumoniae* and similar susceptible microorganisms. The methods of the invention result in a cure of the infection and reversal of the clinical condition. The invention further provides combinations of antimicrobial agents effective against intracellular pathogens including *C. pneumoniae* and other *Chlamydia* species. The invention therefore provides methods and pharmaceutical compositions for the treatment not only of vascular complications of *Chlamydia* infections but also disorders resulting from or aggravated by such infections. Such disorders include asthma, chronic obstructive lung disease, dementia, urinary and gynaecologic mucosal Chlamydial infections.

Thus, the invention provides methods and pharmaceutical compositions for the eradication of persistent *Chlamydia* infections in individuals with disorders that are a manifestation of or contributed to by said infection. These disorders include atherosclerotic vascular disease affecting coronary arteries, aorta, carotid arteries and other arteries including renovascular and glomerular disease, aortic vascular disease, peripheral vascular disease, carotid or cerebrovascular disease, atrial fibrillation and other cardiac arrhythmias, myocardial infarction, unstable or stable angina, valvular heart disease, cardiomyopathy, myocarditis and vasculitis; upper or lower respiratory tract infection; pneumonia; asthma; chronic airflow limitation; sarcoidosis; lung cancer; granulomatous hepatitis; dementia and gynaecologic and urologic mucosal infections.

Further, the methods and pharmaceutical compositions of the invention, in addition to having application for Chlamydial infections, have utility for clinical syndromes that result from infection by mycoplasma, Bartonella, Leptospirosis and Q fever.

In one broad form, the present invention relates to a method of treating patients with a previous or current infection with *C. pneumoniae* and similar susceptible microorganisms by administering a combination of at least one antibiotic or antimicrobial agent and at least a second antibiotic or antimicrobial agent, the first and second antimicrobial agents each being selected from the following class of antibiotics or antimicrobial agents: tetracyclines, macrolides, quinolones, chloramphenicol, rifamycins, sulfonamides, co-trimoxazole and oxazolidinones. A major application of the present invention is for the treatment of patients with, or at risk of, vascular disease following infection with *C. pneumoniae* or similar susceptible microorganisms. However, as disclosed herein above, the invention includes treatment or prevention of other disorders in which *C. pneumoniae* or similar susceptible microorganisms have an aetiological role.

In the methods and pharmaceutical compositions of the invention, the first antibiotic, the second antibiotic and any additional antibiotics are preferably, but not necessarily, selected from different classes of antibiotics as identified herein above. For example, the antibiotics used in a method of the present invention are preferably each selected from different classes wherein the classes are tetracyclines, macrolides, quinolones, chloramphenicol, rifamycins, sulfonamides, co-trimoxazole and oxazolidinones. Similarly, the antibiotics included in a pharmaceutical composition of the present invention are preferably each selected from different classes selected from tetracyclines, macrolides, quinolones, chloramphenicol, rifamycins, sulfonamides, co-trimoxazole and oxazolidinones.

More preferably in the methods and pharmaceutical compositions of the invention the first antibiotic is selected from a macrolide antibiotic and the second antibiotic is selected from tetracyclines and quinolones. Thus, in one form of the second embodiment, the invention provides a pharmaceutical composition for the treatment of a condition associated with infection by *Chlamydia* species or similar susceptible microorganisms in a patient in need of such treatment, the composition comprising a first antibiotic which is a macrolide antibiotic and a second antibiotic or antimicrobial agent which is selected from tetracyclines and quinolones.

More preferably when a three-drug regime is selected for a method of the present invention, then three antibiotics, each being from the following different classes, are selected, where the classes of antibiotics are tetracyclines, macrolides, quinolones, chloramphenicol, rifamycins, sulfonamides, co-trimoxazole and oxazolidinones.

In another form of the second embodiment, the invention provides a pharmaceutical composition for the treatment of a condition associated with infection by *Chlamydia* species or similar susceptible microorganisms in a patient in need of such treatment, the composition comprising at least two different antibiotics or antimicrobial agents selected from the group consisting of tetracyclines, macrolides, quinolones, chloramphenicol, sulfonamides, co-trimoxazole and oxazolidinones and not including a rifamycin.

In still another form of the second embodiment, the invention provides a pharmaceutical composition for the treatment of a condition associated with infection by *Chlamydia* species or similar susceptible microorganisms in a patient in need of such treatment, the composition comprising azithromycin, rifampicin, and doxycycline or a quinolone.

In yet another form of the second embodiment, the invention provides a pharmaceutical composition for the treatment of a condition associated with infection by *Chlamydia* species or similar susceptible microorganisms in a patient in need of such treatment, the composition comprising clarithromycin, rifampicin, and doxycycline.

In a further form of the second embodiment, the invention provides a pharmaceutical composition for the treatment of a condition associated with infection by *Chlamydia* species or similar susceptible microorganisms in a patient in need of such treatment, the composition comprising roxithromycin, ofloxacin and rifampicin.

In the pharmaceutical composition of the third embodiment, preferably the second antibiotic or antimicrobial agent is provided with a pharmaceutically acceptable coating.

In one form of the pharmaceutical composition of the third embodiment, the coating or coatings are adapted to cause the first and second antibiotics or antimicrobial agents to be released in first and second environments in the gastrointestinal tract of a patient to whom the composition is administered, wherein an effective amount of the first antibiotic or antimicrobial agent is capable of being absorbed into the bloodstream of the patient from the first environment and an effective amount of the second antibiotic or antimicrobial agent is capable of being absorbed into the bloodstream of the patient from the second environment.

In another form of the pharmaceutical composition of the third embodiment, the composition further comprises a third antibiotic or antimicrobial agent provided with a third pharmaceutically acceptable coating. Typically, the third coating is adapted to cause the third antibiotic or antimicrobial agent to be released in a third environment in the gastrointestinal tract of a patient to whom the composition is administered, wherein an effective amount of the third antibiotic or antimicrobial agent is capable of being absorbed into the bloodstream of the patient from the third environment.

Preferably, in this form of the pharmaceutical composition of the third embodiment, the first antibiotic or antimicrobial agent is a macrolide, typically an azalide or ketolide, more typically azithromycin, clarithromycin or roxithromycin, the second antibiotic or antimicrobial agent is a rifamycin, typically rifampicin, and the third antibiotic or antimicrobial agent is a tetracycline (typically doxycycline), or a quinolone, typically but not restricted to ofloxacin.

Alternatively, in this form of the pharmaceutical composition of the third embodiment, the first, second and third antibiotics or antimicrobial agents are selected from the group consisting of clarithromycin, rifabutin, rifampicin, azithromycin, roxithromycin, amikacin, clofazimine, ethambutol, ofloxacin, ciprofloxacin and oxazolidinone. More typically in this form the first, second and third antibiotics or antimicrobial agents are clarithromycin, rifabutin and clofazimine. In such a composition, the amount of clarithromycin is typically from 200–300 mg, more typically about 250 mg, the amount of rifabutin is typically from 50–250 mg, more typically about 150 mg, and the amount of clofazimine is typically from 10–150 mg, more typically about 50 mg.

In one particularly preferred method in accordance with the invention there are administered azithromycin in an amount of 500 mg per day, rifampicin in an amount of 300 mg per day, and doxycycline in an amount of 100 mg per day and/or a quinolone; the administration being daily for four weeks.

In another particularly preferred method in accordance with the invention there are administered clarithromycin 500 mg per day, rifampicin 300 mg per day, and doxycycline 100 mg per day; the administration being orally, daily for four weeks.

In a further particularly preferred method in accordance with the invention there are administered roxithromycin 300 mg per day, ofloxacin 400 mg per day, and rifampicin 300 mg per day; the administration being orally, daily for four weeks.

One preferred pharmaceutical composition in accordance with the invention includes azithromycin in an amount of 250 mg, rifampicin in an amount of 150 mg, and doxycycline in an amount of 50 mg.

Another preferred pharmaceutical composition in accordance with the invention includes clarithromycin in an amount of 250 mg, rifampicin in an amount of 150 mg, and doxycycline in an amount of 100 mg.

A further preferred pharmaceutical composition in accordance with the invention includes roxithromycin in an amount of 150 mg, ofloxacin in an amount of 200 mg, and rifampicin in an amount of 150 mg.

Examples of tetracyclines suitable for use in the methods and pharmaceutical compositions of the present invention include tetracycline, oxytetracycline, doxycycline, demeclocycline, chlortetracycline, methacycline and minocycline. Examples of macrolide antimicrobial agents suitable for use in the methods and pharmaceutical compositions of the present invention include erythromycin (including various forms occurring as base, stearate, ethyl succinate, lactobionate, gluceptate and estolate), clarithromycin, azithromycin, roxithromycin, spiramycin, oleandomycin, triacetyloleandomycin, josamycin, kitsamycin, midecamycin, miocamycin, rokitamycin, rosarimycin, flurithromycin dithromycin as well as other azalides and ketolide antibiotics. Examples of quinolone antibiotics suitable for use in the methods and pharmaceutical compositions of the present invention include nalidixic acid, oxolinic acid, norfloxacin, pefloxacin, amifloxacin, ofloxacin, ciporofloxacin, enoxacin, lomefloxacin, fleroxacin, temafloxacin, sparfloxacin, tosulfloxacin, clinafloxacin, cinoxacin, trovafloxacin, levofloxacin, nadifloxacin and refloxacin. Examples of the rifamycin class of antimicrobial agents suitable for use in the methods and pharmaceutical compositions of the present invention include rifampicin, rifabutin and rifapentin. Examples of sulfonamides suitable for use in the methods and pharmaceutical compositions of the present invention include sulfisoxazole, sulfamethoxazole, sulfadiazine, sulfadoxine, sulfasalazine, sulfaphenazole, dapsone, and sulfacytidine, Other classes of antibiotics suitable for use in the methods and pharmaceutical compositions of the present invention include co-trimoxazole and oxazolidinones. Examples of oxazolidinones include linezolid and oxazolidinone.

The doses of the antibiotics or antimicrobial agents used in this invention are in accordance with their generally known and established safe dosage ranges when they are used in monotherapy for the treatment of other conditions.

Such dosages for antibiotics or antimicrobial agents are well known to medical practitioners and range from 0.0005 to 50 g per day, depending on the agent. Safe dosages of antibiotics and antimicrobial agents for use in the methods of the present invention are described, for example, in Martindale, The Extra Pharmacopoeia, Thirty-first Edition (The Royal Pharmaceutical Society, London, 1996). Administration may be by oral, intravenous, intra-arterial, intramuscular, inhalation, topical and subcutaneous routes. Typically, administration is by the oral route. Administration of each of the antibiotics or antimicrobial agents may be in a single daily dose, or in two or more doses per day. Typically the antibiotics or antimicrobial agents are administered to the patient essentially simultaneously, but they need not be.

Pharmaceutical compositions of the present invention typically include the active substances in amounts of from 10% to 100% of the respective daily doses, more typically from 20% to 50% of the daily doses.

Typically, in the methods of the present invention, the combination of first and second antibiotics, and optionally one or more additional antibiotics or antimicrobial agents is administered for between 1 and 28 days. However, the treatment may be continued, as may be indicated in certain clinical circumstances, especially in previously treated patients, for up to 6 months. More prolonged therapy may be indicated in patients who are unable to have initial therapy at adequate doses because of intolerance to any of the antimicrobial agents in the composition, in patients who experience a relapse of their clinical condition, or in patients who have evidence of ongoing inflammation or ongoing inflammatory markers.

Treatment of conditions associated with *C. pneumoniae* is typically continued until the following conditions are established in the patient: peripheral blood PCR detection of *C. pneumoniae* reduced to undetectable levels; normalisation of inflammatory markers including ESR, CRP and serum amyloid A protein; reduction in *C. pneumoniae* IgA titre and reduction in *C. pneumoniae* IgG titre; disappearance of identifiable *C. pneumoniae* from bowel or bronchial biopsies by antigen detection methods or molecular methods; disappearance of *C pneumoniae* from sputum or stool tests by antigen detection methods or molecular methods. Similar diagnostic indicators are utilised for monitoring the effectiveness of a method of treatment of the invention for similar susceptible microorganisms to *C. pneumoniae.*

Preferably the initial treatment is followed by maintenance therapy with intermittent dosing of combined antibiotics on a periodic basis which may range from an additional day or more days per month for additional months or years. In some patients, dormant or persistent organisms may require treatment regimes to be extended for many years.

In one preferred form, the invention provides pharmaceutical compositions presented in a format suitable for specific clinical circumstances. For example, for patients with vascular disease, atypical pneumonia syndromes or pelvic inflammatory disease in particular, these special methods of administration are recommended. As described in more detail below, pharmaceutical compositions of the invention may be provided as single dosage forms which release the active substances into the bloodstream of a patient to whom they are administered in a controlled manner so as to prevent a sudden increase in the plasma concentration of the agents as would occur if they were administered, for example, as separate tablets. Since patients with conditions as exemplified above are often unwell and are often on other therapy, it is envisaged that these enhancements to delivery will reduce adverse experiences by patients including gastrointestinal tract intolerance and will minimise interactions with other concomitant therapy. Combined packaging as described below should also enhance compliance and therefore clinical outcomes.

A pharmaceutical composition of the second or third embodiment may be provided in sequential packaging for each antimicrobial agent or in daily compliance-enhancing packaging in which antimicrobial agents are formulated within a common capsule or tablet. In a further form, a sequence package of medications is provided for intravenous or intramuscular use followed by oral use.

In one form of the method of the first embodiment, the method further comprises the administration of one or more other medications used in the management of coronary and other vascular disease.

In another form of the method of the first embodiment, the method further comprises the administration of one or more other medications that enhance host defence mechanisms important in the eradication of intracellular pathogens.

Preferably the method of the first embodiment, when used for the treatment of patients with cardiovascular disease, further includes the administration of one or more additional agents selected from selective and non-selective cyclooxygenase inhibitors such as aspirin; other antiplatelet drugs such as ticlodipine or clopidogrel; betablockers; antiarrhythmics; calcium channel blockers, other anticoagulant drugs such as coumadin or heparin: nitrate medicines and HMG-Coareductase inhibitors. Examples of betablockers include inderal, metoprolol and atenolol; examples of antiarrhythmics include amiodarone, lignocaine, sotalol and flecanide; examples of calcium channel blockers include amlodipine, diltiazem and verapamil; examples of nitrate medicines include isosorbide mononitrate and nitroglycerin.

The methods of treatment of the first embodiment, when used for the treatment of patients who may have persistent *Chlamydia* infection, may further include the administration of one or more immune response modifiers selected from cytokines, including interleukin 1, interleukin 2, interleukin 3, interleukin 4, interleukin 5, interleukin 6, interleukin 7, interleukin 8, interleukin 9, interleukin 10, interleukin 11, interleukin 12, interleukin 13, interleukin 14, interleukin 15, interleukin 16, interleukin 17, interleukin 18, interleukin 19, interleukin 20; colony stimulating factors including G-CSF, GM-CSF; tumour necrosis factors alpha and beta; interferon alpha, beta and gamma: peptides which bind to macrophage and lymphocyte surface receptors; glycoproteins which mimic cytokines; and other mediator molecules.

The methods of treatment of the first embodiment may further include the administration of one or more other drugs with immunosuppressive activity when active inflammation or inappropriately biased and deleterious host immune responses are present. Examples of suitable drugs with immunosuppressive activity include prednisone and related steroids, azathioprine, mofetil mycofenolate and related purine antagonists, cyclophosphamide and related alkylating agents, methotrexate and related folate antagonists, thalidomide, chloroquine and related antimalarial compounds, levamisole, cyclosporin A and similar immunosuppressive agents including rapamycin and FK506.

Similarly, the pharmaceutical composition of the second and third embodiments may further include one or more other medications used in the management of coronary and other vascular disease and/or one or more other medications that enhance host defence mechanisms important in the eradication of intracellular pathogens, such medications being as further described herein above.

Dosages of further agents, such as those exemplified herein above, when used in the methods of the present invention, are in accordance with their generally known and established safe dosage ranges. Such dosages are well known to medical practitioners and are described, for example, in Martindale, The Extra Pharmocopoeia, Thirty-first Edition (The Royal Pharmaceutical Society, London, 1996).

In the methods of the invention, each of the co-administered antibiotics or antimicrobial agents may be administered to and ingested by the patient as separate medications, for example in the form of separate tablets, capsules or sachets, or as separate intravenously administered agents. Such tablets or capsules may be packaged and administered to the patient, for example, in a compliance-enhancing package of separate containers. Alternatively, separate tablets, capsules, etc, may be packaged in blister packs designed to guide the patient to compliance with the dosing protocol. For example, where a method of the invention involves the administration of three different medications a blister pack may be constructed to house the three different medications on the blister pack in such a manner as to direct the patient to a morning dose of each of the three medications, a midday dose of two of the medications, and an evening dose of the three medications again. In such an arrangement, each blister pack strip of medications could constitute a day's therapy, thereby enhancing the likelihood of patient compliance. Other variations of the arrangement described, according to the desired dosage protocol, will readily suggest themselves.

Alternatively, to further simplify administration of the medications to the patient and the patient's compliance with the dosage protocol, the combination of medications may be provided as microparticles or microgranules, typically micro-encapsulated, and a predetermined mass of each drug, preferably in its micro-encapsulated form, may be included in a single capsule or tablet. Alternatively, the medications may be formulated into separate tablets or capsules which are then incorporated into a single larger tablet or capsule as the final dosage form. In this manner the combination of two, three or more antimicrobial agents described above optionally together with one or more other medications as described above may be combined into a single dosage form to simplify the medication process and to delivery special dose combinations not currently available in the size tablets and capsules currently on the market.

Pharmaceutical compositions of the second or third embodiments may include one or more pharmaceutically acceptable excipients, adjuvants, diluents or carriers which are generally known in the art.

Pharmaceutical compositions of the second embodiment or for administration in a method of the first embodiment may be prepared by means known in the art for the preparation of pharmaceutical compositions including blending, grinding, homogenising, suspending, dissolving, emulsifying, dispersing and where appropriate, mixing of the active agents, optionally together with one or more excipients, diluents, carriers and adjuvants.

For oral administration, a pharmaceutical composition of the second embodiment may be in the form of tablets, lozenges, pills, troches, capsules, elixirs, powders, including lyophilised powders, solutions, granules, suspensions, emulsions, syrups and tinctures. Slow-release, or delayed-release, forms may also be prepared, for example in the form of coated particles, multi-layer tablets or microgranules.

Solid forms for oral administration may contain pharmaceutically acceptable binders, sweeteners, disintegrating agents, diluents, flavourings, coating agents, preservatives, lubricants and/or time delay agents. Suitable binders include gum acacia, gelatin, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lacrose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, ion addition to the active agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further include dispersing agents and/or suspending agents. Suitable suspending agents include sodium carboxymethylcellulose, methylcellulose, hydroxypropylmethyl-cellulose, poly-vinyl-pyrrolidone, sodium alginate or cetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Emulsions for oral administration may further include one or more emulsifying agents. Suitable emulsifying agents include dispersing agents as exemplified above or natural gums such as gum acacia or gum tragacanth.

In the pharmaceutical compositions of the third embodiment, coatings are applied to the medications preferably to deliver the antimicrobial agents differentially to different regions of the gastrointestinal tract. The coatings may be applied, for example, to tablets of the medications which are then incorporated into a single dosage form such as a tablet or capsule. As another possibility the coatings may be applied in a micro-encapsulation process and the microencapsulated medications formulated into tablets or capsules so as to provide all of the microencapsulated medications in a single dosage form. For example, the antimicrobial agents may be coated, for instance by microencapsulation, so that they are released at different rates in the gastric lumen, the distal duodenum and beyond—so enhancing absorption and reducing cross-section between the medications. Typically, in this form, an antibiotic or antimicrobial agent is provided with a coating which maximises its release in a part of the gastrointestinal tract in which it is most effectively absorbed, and which minimises its release in other parts of the gastrointestinal tract.

For example, in a composition containing azithromycin, rifampicin and doxycycline, the azithromycin may be microencapsulated so as to dissolve in the gastric acidic environment while the other two actives are microencapsulated so as to be substantially undissolved in that environment, the doxycycline being coated so that it is released in the conditions within the second part of the duodenum, and the rifampicin being coated so that it is released more distally. In such a way the agents are released into environments in which they are readily absorbed and the possibility of them cross-reacting is minimised.

As a further possibility, a pharmaceutical composition of the third embodiment may be provided as a multilayer dosage form, in which the antibiotics or antimicrobial agents are provided in separate layers, or as a core and one or more separate layers, the active substances being separated by at least one coating so that an active substance provided in an outer layer is released first into the bloodstream of a patient in an appropriate region of the gastrointestinal tract, and one or more other antibiotics or antimicrobial agents in one or more inner layers are released subsequently, when the first active has been substantially released and a coating which separates it from the other active or actives has dissolved or been eroded.

The regions of the gastrointestinal tract in which antibiotics or antimicrobial agents used in the methods or compositions of the present invention are most effectively absorbed are generally known in the art. Similarly, suitable coatings for pharmaceutically active substances to delay release of the substances until they reach predetermined environments within the gastrointestinal tract are generally known in the art, as are techniques for microencapsulation with such materials. Examples of references describing such coatings and techniques are Kirk-Othmer's Encyclopedia of Chemical Technology, Fourth Edition, Volume 7, pp 274–300(Wiley-Interscience, 1993) and references cited therein; Remington's Pharmaceutical Sciences, 18$^{th}$ Edition, Chapters 90 and 91 (Mack Publishing Company, Easton, Pa., 1990) and references cited therein; Australian Patent numbers 601974 and 603568 and references cited therein; and U.S. Pat. Nos. 5,914,132, 5,910,322 and 588,550, and references cited therein. Other relevant references include the following:

Ranade, V. V., *J. Clin. Pharmacol.*, 1991, 31, 2–16;

Smart, J. D., et al., *J. Pharm. Pharmacol.*, 1984, 36, 295;

Hovgaard, L. and Brondsted, H., *Crit. Rev. Ther. Drug Carrier Syst.*, 1996 13, 185–223; and Leopold, C. S., *Pharm. Sci. Technol. Today*, 1999, 2, 197–204.

The disclosures of each of the references cited above are incorporated herein by reference.

Examples of coatings for targeting release of a pharmaceutical substance in the stomach include modified celluloses such as hydroxymethyl cellulose and hydroxypropyl cellulose, polysaccharide gums, tragacanth gum, sodium carboxymethylcellulose, chitosan, acrylates and methacrylates. Where it is desired for an antibiotic or antimicrobial agent of a pharmaceutical composition of the invention to be released in the stomach, the antibiotic or antimicrobial agent need not be provided with a coating. Coating for targeting release of an antibiotic or antimicrobial agent of a pharmaceutical composition of the invention in the stomach may be, for instance, be polymers available from Röhm GmbH, Germany, and sold under the Trade Marks Eudragit E, Eudragit RL and Eudragit RS.

Examples of coatings for targeting release of a pharmaceutical substance in the lower intestine include enteric coatings such as methacrylic acid copolymers, cellulose acetate phthalate, cellulose acetate succinate and styrol maleic copolymers (Agyilirah, G. A., et al., in Polymers for Controlled Drug Delivery, pp 39–66; Tarcha, P. J. ed., CRC Press. Boca Raton (1991)).

Examples of coatings for targeting release of a pharmaceutical substance in the colon include pH resistant polymeric coatings such as Eudragit L. and Eudragit S and bioerodable polymers such as shellac, ethyl cellulose, cellulose acetate phthalate and modified cellulose phthalates such as hydroxypropyl methylcellulose phthalate, cellulose acetate trimellitate, poly(vinyl acetate/vinyl alcohol) phthalate and cellulose acetoacetate mixed esters (U.S. Pat. No. 5,811,121).

Coatings may be applied to the active substances from solution in organic solvents or aqueous organic solvents. The coatings my include additives such as plasticisers, for example phthalic acid esters such as dibutyl phthalate, triacetin, fatty alcohols such as cetyl alcohol, citric acid esters, dibutyl succinate and the like; particulate dispersants such as talc and titanium dioxide; and colorants such as metal oxides or dyes. Solvents which may be used include methanol, ethanol, isopropanol, acetone, dichloromethane, diethyl ether, ethyl acetate and mixtures thereof. The choice of solvent is determined primarily by the solubility of the polymer and ease of evaporation of the solvent. Selection and amount of solvent, optional plasticiser, optional inert solid particulate and process of coating is made based upon the specific coating material used according to criteria known to those skilled in the relevant art. Coating methods are known to persons of ordinary skill in the relevant art and may utilise equipment such as fludised beds, perforated pans, and spray equipment.

EXAMPLES

Example 1:

Treatment of patients with coronary heart disease

Ten patients, aged 48–75, had had myocardial infarction and received acute therapy with thrombolytic agents. They subsequently proceeded to coronary angiography and subsequently stenting or coronary artery bypass surgery. Baseline cholesterol values were relatively low at less than 5.5 mmol/L. Despite good conventional management each patient developed recurrent angina within 12 months of revascularisation, documented by exercise Sestamibi testing. Serological testing by microimmunofluorescence assays and ELISAs confirmed "persistent" infection with *C. pneumoniae* with elevated IgA and IgG antibodies. The patients were treated with a combination of rifampicin 300 mg bd, doxycycline 100 mg twice daily as well as roxithromycin 150 mg twice daily for one month. Symptoms of ischaemic heart disease diminished following therapy and progress exercise Sestamibi studies confirmed improvement. Eighteen months later, no patients have had recurrence of their disease or progression of their disease. Assays of peripheral blood mononuclear cells showed a reduction in detectable *C. pneumoniae* DNA (by PCR) after therapy and specific IgA antibodies declined.

Example 2:
Treatment of patients with atypical pneumonia and atrial fibrillation.

Three patients, aged 40–72, had ben admitted to hospital with fever, cough and dyspnoea. They had clinical and radiological signs of bilateral pneumonia and evidence of significant hypoxia on arterial blood gas studies. In each patient, the pneumonia was investigated by acute and convalescent phase serology and found to be due to *C. pneumoniae*. All patients had recent onset atrial fibrillation. The patients received treatment with doxycycline 100 mg bd and azithromycin 500 mg twice daily for three weeks. In each patient, atrial fibrillation resolved within one week and pneumonia resolved within three weeks. One year later, no patient has had a recurrence of atrial fibrillation.

Example 3:
Treatment of patients with vascular disease, *C. pneumoniae* infection and cancer One patient, a 68 year old male had had bilateral carotid endarterectomies. Two years later he developed common bile duct obstruction. One year later he was diagnosed with cancer of the head of pancreas with hepatic metastases. He had a palliative small bowel anastomosis. He developed angina. He was found to have persisting IgA and IgG antibodies to *C. pneumoniae* by microimmunofluorescence testing. He declined cytotoxic chemotherapy for his pancreas cancer. He began therapy with 3 million units of interleukin-2 (subcutaneous 4 days every month) killed *Mycobacterium w* ($10^7$ organisms sc) and combined antibiotics including doxycycline 100 mg daily (three weeks) and roxithromycin 150 mg bd (three weeks). The metastatic lesions of pancreatic cancer regressed by more than 80% after three months of therapy. His CA19-9 returned to an undetectable level. Circulating CD4 T cells had not expressed TNF or gamma-interferon prior to cytokine therapy were found to have cytoplasmic expression of TNF and gamma-interferon three months after cytokine therapy. His angina ceased without ECG changes and did not recur. He remains well three years later, without angina, with no evidence of vascular disease and has no evidence of metastases on PET scans. IgA *C. pneumoniae* serology is negative.

Example 4
Pharmaceutical composition

The following is illustrative of a pharmaceutical composition in accordance with the invention.

Coating of doxycycline

A solution of Eudragit L100-55 (100 parts by weight) and dibutyl phthalate (20parts by weight) is prepared in isopropanol:acetone:water (37:9:1 by weight; 1000 parts by weight) and micronised talc (40 parts by weight) is suspended in the solution. The solution is coated onto a finely pulverised commercial preparation of doxycycline including lactose as inert (200 parts by weight) in a perforated pan coater maintaining an outlet air/bed temperature of about 30° C.

Coating of rifampicin

A solution of hydroxypropyl methylcellulose phthalate (100 parts by weight) and cetyl alcohol (5 parts by weight) in acetone:ethanol (2.5:1 by weight, 1300 parts by weight) is sprayed onto a finely pulverised commercial preparation of rifampicin containing lactose as inert (200 parts by weight) in a fluidised bed apparatus with spray guns placed above the bed.

Preparation of pharmaceutical composition in dosage form

Azithromycin, coated rifampicin and coated doxycycline in proportions of 5:3:1 by weight of active substances are blended and portions of the blend are encapsulated into gelatin capsules each containing 125 mg azithromycin, 75 mg rifampicin and 25 mg doxycycline.

What is claimed is:

1. A method for the treatment or prevention of a condition associated with infection by microorganisms selected from the group consisting of *chlamydia* species, *mycoplasma* species, *listeria* species, *bartonella* species, and the aetiologic agents of leptospirosis and Q fever in a patient in need of such treatment or prevention, the method comprising the administration to the patient of an effective amount of at least two different antibiotics or antimicrobial agents selected from the group consisting of tetracyclines, macrolides, quinolones, rifamycins, sulfonamides, co-trimoxazole and oxazolidinones.

2. A method according to claim 1 which further includes the administration of a third, or a third and a fourth, or a third, a fourth and one or more further different antimicrobial agents or antibiotics.

3. A method for the treatment or prevention of a condition associated with infection by microorganisms selected from the group consisting of *Chlamydia* species, *Mycoplasma* species, *Listeria* species, *Bartonella* species, and the aetiologic agents of leptospirosis and Q fever in a patient in need of such treatment or prevention, the method comprising the administration to the patient of an effective amount of at least three different antibiotics, each antibiotic being from a different class, selected from the group consisting of tetracyclines, macrolides, quinolones, chloramphenicol, rifamycins, sulfonamides, co-trimoxazole and oxazolidinones.

4. A method according to claim 1 wherein one antibiotic is a macrolide antibiotic and another antibiotic is selected from tetracyclines and quinolones.

5. A method according to claim 1 comprising administration of azithromycin, rifampicin and a third antibiotic selected from doxycycline and the quinolones.

6. A method according to claim 1 further comprising the administration of one or more further agents selected from other medications used in the management of coronary and other vascular disease, other medications that enhance host defence mechanisms important in the eradication of intracellular pathogens, selective and non-selective cyclooxygenase inhibitors; other antiplatelet drugs; betablockers; anti-arrhythmics; calcium channel blockers; other anticoagulant drugs; nitrate medicines and HMG-Coareductase inhibitors; immune response modifiers selected from cytokines; colony stimulating factors; tumour necrosis factors alpha and beta; interferon alpha, beta and gamma; peptides which bind to macrophage and lymphocyte surface receptors: glycoproteins which mimic cytokines; and other mediator molecules; prednisone and related steroids, azathioprine, mofetil mycofenolate and related purine antagonists, cyclophosphamide and related alkylating agents, methotrexate and related folate antagonists, thalidomide, chloroquine and related antimalarial compounds, levamisole, cyclosporin A, rapamycin and FK506.

7. A method according to any one of claims 1–6 wherein said condition is selected from atherosclerotic vascular disease affecting coronary arteries, aorta, carotid arteries and other arteries, renovascular and glomerular disease, aortic vascular disease, other cardiac arrhythmias, myocardial infarction, unstable and stable angina, valvular heart disease, cardiomyopathy, myocarditis and vasculitis, upper and lower respiratory tract infection, pneumonia, asthma, chronic airflow limitation, sarcoidosis, lung cancer, granulomatous hepatitis, dementia and gynaecologic and urologic mucosal infections, clinical syndromes that result from infection by mycoplasma, Bartonella, Leptospirosis and Q fever.

8. A method according to any one of claims 1–6 for the treatment or prevention of a condition associated with *Chlamydia pneumoniae* infection.

9. At least two different antibiotics or antimicrobial agents selected from the group consisting of tetracyclines, macrolides, quinolones, rifamycins, sulfonamides, co-trimoxazole and oxazolidinones, when used for the treatment or prevention of a condition associated with infection by microorganisms selected from the group consisting of *Chlamydia* species, *Mycoplasma* species, *Listeria* species, *Bartonella* species, and the aetiologic agents of leptospirosis and Q fever in a patient in need of such treatment.

10. A pharmaceutical composition for the treatment of a condition associated with infection by microorganisms selected from the group consisting of *Chlamydia* species, *Mycoplasma* species, *Listeria* species, *Bartonella* species, and the aetiologic agents of leptospirosis and Q fever in a patient in need of such treatment, the composition comprising at least two different antibiotics or antimicrobial agents selected from the group consisting of tetracyclines, macrolides, chloramphenicol, rifamycins, sulfonamides, co-trimoxazole and oxazolidinones, with the proviso that said composition is not a composition which includes both chloramphenicol and a tetracycline, said pharmaceutical composition being suitable for oral administration.

11. A pharmaceutical composition according to claim 10 which further includes a third, or a third and a fourth, or a third, a fourth and one or more further different antimicrobial agents or antibiotics.

12. A pharmaceutical composition according to claim 10 wherein one antibiotic is a macrolide antibiotic and another antibiotic is selected from tetracyclines.

13. A pharmaceutical composition according to claim 10 comprising at least three different antibiotics, each antibiotic being from a different class, selected from tetracyclines, macrolides, quinolones, chloramphenicol, sulfonamides, co-trimoxazole and oxazolidinones.

14. A pharmaceutical composition for the treatment of a condition associated with infection by microorganisms selected from the group consisting of *Chlamydia* species, *Mycoplasma* species, *Listeria* species, *Bartonella* species, and the aetiologic agents of leptospirosis and Q fever in a patient in need of such treatment, the composition comprising at least two different antibiotics or antimicrobial agents selected from the group consisting of tetracyclines, macrolides, chloramphenicol, sulfonamides, co-trimoxazole and oxazolidinones and not including a rifamycin; with the proviso that said composition is not a composition which includes both chloramphenicol and a tetracycline; said composition being suitable for oral administration.

15. A pharmaceutical composition for the treatment of a condition associated with infection by microorganisms selected from the group consisting of *Chlamydia* species, *Mycoplasma* species, *Listeria* species, *Bartonella* species, and the aetiologic agents of leptospirosis and Q fever in a patient in need of such treatment, the composition comprising a first antibiotic or antimicrobial agent selected from the group consisting of azithromycin, clarithromycin and roxithromycin, a second antibiotic or antimicrobial agent which is rifampicin, and a third antibiotic or antimicrobial agent selected from doxycycline and ofloxacin, said composition being suitable for oral administration.

16. A pharmaceutical composition according to any one of claims 10, 14 or 15 further comprising one or more other medications used in the management of coronary and other vascular disease.

17. A pharmaceutical composition according to any one of claims 10, 14 or 15 further comprising one or more other medications that enhance host defence mechanisms important in the eradication of intracellular pathogens.

18. A pharmaceutical composition according to any one of claims 10, 14 or 15 further comprising one or more additional agents selected from selective and non-selective cyclooxygenase inhibitors; other antiplatelet drugs; betablockers; antiarrhythmics; calcium channel blockers; other anticoagulant drugs; nitrate medicines and HMG-Coareductasc inhibitors.

19. A pharmaceutical composition according to any one of claims 10, 14 or 15 further comprising one or more immune modifiers selected from cytokines; colony stimulating factors; tumour necrosis factors alpha and beta; interferon alpha, beta and gamma; peptides which bind to macrophage and lymphocyte surface receptors; glycoproteins which mimic cytokines; and other molecules.

20. A pharmaceutical composition according to any one of claims 10, 14 or 15 further comprising one or more drugs with immunosuppressive activity selected from prednisone and related steroids, azathioprine, mofetil mycofenolate and related purine antagonists, cyclophosphamide and related alkylating agents, methotrexate and related folate antagonists, thalidomide, chloroquine and related antimalarial compounds, levamisole, cyclosporin A, rapamycin and FK506.

21. A pharmaceutical composition according to any one of claims 10, 14 or 15, wherein said antimicrobial agents are formulated within a single capsule or tablet.

22. A pharmaceutical composition according to any one of claims 10, 14 or 15, wherein said antibiotics or antimicrobial agents are microencapsulated.

23. A pharmaceutical composition according to claim 22 wherein said microencapsulation is adapted to cause said antibiotics or antimicrobial agents to be released differentially in different regions of the gastrointestinal tract.

24. A pharmaceutical composition comprising a first antibiotic or antimicrobial agent provided with a first pharmaceutically acceptable coating and at least a second antibiotic or antimicrobial agent optionally provided with a second pharmaceutically acceptable coating, said antibiotics or antimicrobial agents being selected from the group consisting of tetracyclines, macrolides, quinolones, chloramphenicol, rifamycins, sulfonamides, co-trimoxazole and oxazolidinones; with the proviso that said composition is not a composition which includes both chloramphenicol and a tetracycline.

25. A pharmaceutical composition according to claim 24, wherein said coating or coatings are adapted to cause said first and second antibiotics or antimicrobial agents to be released in first and second environments in the gastrointestinal tract of a patient to whom said composition is administered, wherein an effective amount of said first antibiotic or antimicrobial agent is capable of being absorbed into the bloodstream of said patient from said first environment and an effective amount of said second antibiotic or antimicrobial agent is capable of being absorbed into the bloodstream of said patient from said second environment.

26. A pharmaceutical composition according to claim 25 further comprising a third antibiotic or antimicrobial agent provided with a third pharmaceutically acceptable coating, said third coating being adapted to cause said third antibiotic or antimicrobial agent to be released in a third environment in the gastrointestinal tract of a patient to whom said composition is administered, wherein an effective amount of said third antibiotic or antimicrobial agent is capable of being absorbed into the bloodstream of said patient from said third environment.

27. A pharmaceutical composition according to claim 26 wherein said first antibiotic or antimicrobial agent is a macrolide, said second antibiotic or antimicrobial agent is a rifamycin, and said third antibiotic or antimicrobial agent is a tetracycline or a quinolone.

28. A pharmaceutical composition according to claim 27 wherein said first antibiotic or antimicrobial agent is selected from azithromycin, clarithromycin and roxithromycin, said second antibiotic or antimicrobial agent is rifampicin, and said third antibiotic or antimicrobial agent is selected from doxycycline and ofloxacin.

29. A pharmaceutical composition according to claim 24 wherein said coatings are applied by microencapsulation.

30. A pharmaceutical composition according to claim 25 wherein said first and second environments are different.

31. A pharmaceutical composition according to claim 26 wherein said first, second and third environments are different.

* * * * *

UNITED STATES PATENT AND TRADEMARK OFFICE
CERTIFICATE OF CORRECTION

PATENT NO.    : 6,475,518 B1                                                Page 1 of 1
DATED         : November 5, 2002
INVENTOR(S)   : Karl William Baumgart et al.

It is certified that error appears in the above-identified patent and that said Letters Patent is hereby corrected as shown below:

Column 14,
Lines 22 and 23, change "chlamydia species, mycoplasma species, listeria species, bartonella species" to -- Chlamydia species, Mycoplasma species, Listeria species, Bartonella species --.

Column 16,
Line 34, after "other" insert -- mediator --.

Signed and Sealed this

Twenty-fifth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,475,518 B1
DATED : November 5, 2002
INVENTOR(S) : Karl William Baumgart et al.

It is certified that error appears in the above-identified patent and that said Letters Patent is hereby corrected as shown below:

<u>Title page,</u>
Item [22], PCT Filed:, change "June 20, 1999" to -- June 30, 1999 --

Signed and Sealed this

Nineteenth Day of August, 2003

JAMES E. ROGAN
*Director of the United States Patent and Trademark Office*